United States Patent [19]

Fleck et al.

[11] 4,179,578

[45] Dec. 18, 1979

[54] PARA-PHENYL STILBENE DERIVATIVES

[75] Inventors: Fritz Fleck, Bottmingen; Hans Kittl, Riehen; Salvatore Valenti, Bottmingen, all of Switzerland

[73] Assignee: Sandoz Ltd., Basel, Switzerland

[21] Appl. No.: 787,510

[22] Filed: Apr. 14, 1977

Related U.S. Application Data

[60] Division of Ser. No. 596,287, Jul. 16, 1975, Pat. No. 4,032,558, which is a continuation of Ser. No. 316,448, Dec. 19, 1972, abandoned.

[30] Foreign Application Priority Data

Dec. 24, 1971 [CH] Switzerland ............... 18907/71
Jan. 26, 1972 [CH] Switzerland ............... 1123/72

[51] Int. Cl.² ............... C07C 63/60; C07C 69/76

[52] U.S. Cl. ............... 560/76; 560/59; 560/83; 560/86; 560/89; 560/102; 562/469; 562/488; 562/492

[58] Field of Search ............... 560/102, 76, 83, 86, 560/89, 64, 65, 73, 87, 59; 260/515 P, 515 R, 520 E, 515 A; 562/492, 488, 469

[56] References Cited

U.S. PATENT DOCUMENTS

| | | | |
|---|---|---|---|
| 3,429,877 | 2/1969 | Maeder et al. | 260/515 R |
| 3,822,305 | 7/1974 | Pintschovius et al. | 260/515 P |
| 4,008,266 | 2/1977 | Intille | 260/515 P |

*Primary Examiner*—Jane S. Myers
*Attorney, Agent, or Firm*—Gerald D. Sharkin; Richard E. Vila; Thomas C. Doyle

[57] ABSTRACT

Stilbene derivatives having at least one further phenyl substituent in the para-position to a benzene ring in the stilbene are optical brighteners particularly suitable for incorporation on spinning masses.

5 Claims, No Drawings

PARA-PHENYL STILBENE DERIVATIVES

This is a division of application Ser. No. 596,287, filed July 16, 1975, now U.S. Pat. No. 4,032,558, which in turn is a continuation, of application Ser. No. 316,448, filed Dec. 19, 1972, now abandoned.

This invention concerns new stilbene derivatives.

The invention provides compounds of formula I,

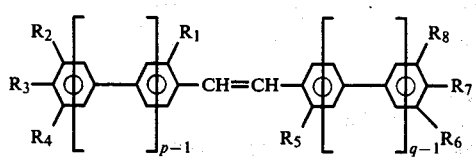

in which $R_1$ and $R_5$ each signifies hydrogen, nitrile, or linear alkyl of 1 to 4 carbon atoms, $R_2$, $R_4$, $R_6$ and $R_8$ each signifies hydrogen, one of the following first-order substituents: halogen, alkyl or alkoxy of 1 to 8 carbon atoms, alkenyl of 3 to 8 carbon atoms, or one of the following second-order substituents: —CN, —COOR', —CONR'R", —SO$_3$R''', —SO$_2$NR'R" or SO$_2$R'''', in which R' signifies hydrogen, alkyl of 1 to 22 carbon atoms, hydroxyalkyl of 2 to 4 carbon atoms, phenyl or methyl- or chlorine-substituted phenyl, R" signifies hydrogen, alkyl of 1 to 8 carbon atoms or hydroxylalkyl of 2 to 4 carbon atoms, or R' and R" together with the vicinal nitrogen atom form a pyrrolidine, piperidine, piperazine or morpholine ring, R''' signifies phenyl or methyl- or chlorine-substituted phenyl, R'''' signifies alkyl of 1 to 4 carbon atoms, phenyl or methyl- or chlorine-substituted phenyl, $R_3$ and $R_7$ each signifies hydrogen, a first-order or second-order substituent as defined above or a heterocycle of formula,

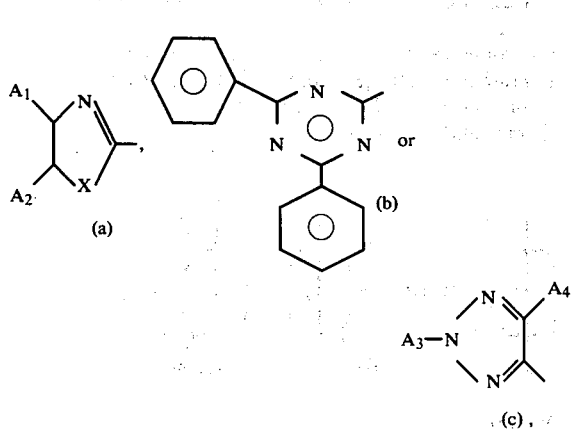

in which

X signifies —O—, —S—, —NH— or —NR''''',

R''''' signifies alkyl of 1 to 4 carbon atoms or hydroxyalkyl of 2 to 4 carbon atoms, $A_1$ and $A_2$ each signifies, if X signifies —O—, phenyl or phenyl substituted by chlorine or alkyl or alkoxy of 1 to 4 carbon atoms, or if X signifies —O—, —S—, —NH— or —NR''''', they together form the atoms of a condensed naphthalene nucleus, a condensed benzene ring or a condensed benzene ring substituted by fluorine, chlorine, nitrile, alkyl of 1 to 8 carbon atoms and/or alkoxy of 1 to 8 carbon atoms, and $A_3$ signifies phenyl or phenyl substituted by one of the named first-order substituents or by a second-order substituent which does not contain a heterocyclic radical, $A_4$ signifies hydrogen or methyl p signifies an integer from 1 to 3 and q signifies an integer from 1 to 3, provided that the total of p and q is at least 3, the total of p and q and the number of second-order substituents in the molecule is at least 5, the heterocycle significances (a), (b) and (c) for $R_3$ and $R_7$ and the —CN significance for $R_1$ or $R_5$ being considered as second-order substituents, and if one of the substituents $R_3$ and $R_7$ is a heterocycle (a), (b) or (c), either the total of p and q is at least 4 and/or at least two further non-heterocyclic second-order substituents are present in the molecule.

The alkyl radicals (first-order substituents) occurring in the compounds of formula I may be, for example, methyl, ethyl, n-propyl, iso-propyl, n-butyl, iso-butyl, tert. butyl, n-amyl, tert. amyl, iso-amyl, sec. amyl, n-hexyl, n-octyl, iso-octyl and 2-ethylhexyl. Only linear radicals with 1 to 4 carbon atoms are suitable as alkyl radicals $R_1$ and $R_5$, i.e. methyl, ethyl, n-propyl and n-butyl. Generally the lower radicals containing 1 to 4 carbon atoms are preferred, while methyl is preferred as the significance of $R_1$ and $R_5$.

The following may be named as examples of alkenyl and alkoxy first-order substituents: allyl, 1-, 2- and 3-butenyl, 1-hexenyl, methoxy, ethoxy, n-propoxy, n-butoxy, tert. butoxy, n-hexyloxy and 2-ethylhexyloxy, of which alkoxy radicals containing 1 to 4 carbon atoms, in particular methoxy, are preferred.

The halogen atoms in the compounds of formula I may be fluorine or preferably chlorine atoms, while as reactive halogen atoms in the intermediates described hereinafter, chlorine, bromine and possibly iodine atoms are of prime interest.

As examples of "non-heterocyclic" second-order substituents, i.e. second-order substituents with the exception of the heterocycles (a), (b) and (c), the following may be named: the nitrile group, the carboxyl group, carboxylic acid alkyl ester in which the alkyl radical contains 1 to 22 or preferably 1 to 8 carbon atoms, e.g. carboxylic acid methyl, ethyl, propyl, iso-propyl, butyl, amyl, hexyl, iso-octyl, n-decyl, n-dodecyl, cetyl, stearylester groups, carboxylic acid β-hydroxyethyl, β-hydroxypropyl, phenyl, p-chlorophenyl, p-methylphenyl, 2,4-dimethylphenyl and 2,5-dichlorophenylester groups, sulphonic acid phenyl, p-chlorophenyl, 2,5-dichlorophenyl, p-methylphenyl and 2,4-dimethylphenylester groups, methyl, ethyl, n-propyl, iso-propyl, n-butyl, iso-butyl, tert. butyl, phenyl, p-chlorophenyl, p-methyl phenyl, 2,4-dimethylphenyl and 2,4,6-trimethylphenylsulphone groups, the free carboxylic and sulphonic acid amide groups and carboxylic acid and sulphonic acid amide groups derived, for example, from the following amines: methyl, ethyl, propyl, butyl, tert. butyl, amyl, iso-amyl, hexyl, octyl, lauryl, dimethyl, diethyl, ethanol-amine and diethanol-amine, N-methyl-N-ethylamine, N-methyl-N- propylamine, aniline, toluidine, xylidine, p-chloroaniline, N-methylaniline, pyrrolidine, piperidine, piperazine and morpholine.

Of the aforenamed second-order substituents, the following are preferred: —CN, the alkylsulphone groups, —SO$_2$—C$_6$H$_5$, —SO$_3$—C$_6$H$_5$, —CONH$_2$, —CO—NHCH$_3$, —CO—N(CH$_3$)$_2$, —CO—N(C$_2$H$_5$)$_2$, —CO—N(CH$_2$CH$_2$OH)$_2$, —CO—NH—CH$_2$CH$_2$OH, the carboxylic acid alkylester groups (preferably carboxylic acid alkyl (1–4 ester groups), —SO$_2$NH$_2$, —SO$_2$NHCH$_3$, —SO$_2$N(CH$_3$)$_2$ and —SO$_2$NHC$_6$H$_5$.

In addition to the stated substituents, the heterocyclic substituents of formulae (a), (b) and (c) are suitable as substituents R$_3$ and R$_7$. In the radical of formula (a), X signifies sulphur, alkylimino or hydroxyalkyl-imino, where alkyl contains 1 to 4 carbon atoms and hydroxyalkyl contains 2 to 4 carbon atoms (e.g. methyl, ethyl, n-propyl, iso-propyl, n-butyl, tert. butyl, β-hydroxyethyl or β-hydroxypropylimino) or, preferably, oxygen. If X signifies oxygen, A$_1$ and A$_2$ may each have, for example, one of the following meanings: phenyl, 4-methyl-, 2,4-dimethyl-, 3,4-dimethyl-, 4-ethyl-, 4-butyl-, 4-methoxy-, 4-ethoxy- or 3-methyl-4-methoxyphenyl. If A$_1$ and A$_2$ form jointly a condensed ring, this may be an unsubstituted naphthalene ring or a benzene ring which may bear, preferably in one or optionally in each of the 5 and 6 positions of the benzoxazole ring, preferably one of the following substituents: methyl, ethyl, n-propyl, n-butyl, methoxy, ethoxy, n-butoxy, tert. butoxy, chlorine or —CN.

As radical A$_3$ unsubstituted phenyl or phenyl substituted by any of the aforenamed first-order substituents or non-heterocyclic second-order substituents is suitable. A$_3$ signifies preferably phenyl or p-chlorophenyl.

The total of p and q may be 3 to 6, but compounds of formula I in which the total of p and q is 4, 5 or 6 are preferred.

The following compounds are especially preferred in view of their properties as optical brightening agents.

Compounds of formula XVI,

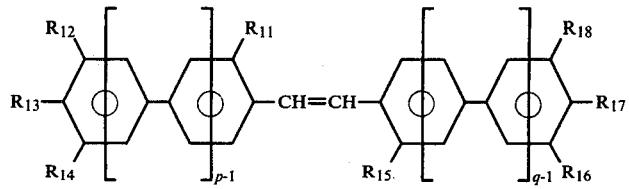

in which
p and q are as defined above,
R$_{11}$ and R$_{15}$ each signifies hydrogen, methyl or —CN, preferably hydrogen or —CN,
R$_{13}$ and R$_{17}$ each signifies hydrogen or a non-heterocyclic second-order substituent, preferably —CN, an alkyl- or phenyl-sulphone group or a carboxylic acid amide or ester group,
R$_{12}$, R$_{14}$, R$_{16}$ and R$_{18}$ each signifies a first-order substituent or preferably hydrogen,
and where the molecule contains 2 to 4 second-order substituents.

Compounds of formula XVII,

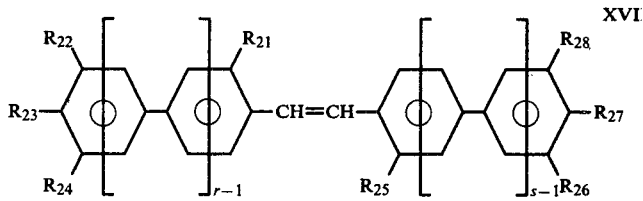

where
R$_{21}$ and R$_{25}$ each signifies hydrogen, methyl or cyano, preferably hydrogen or cyano,
R$_{22}$, R$_{24}$, R$_{26}$ and R$_{28}$ each signifies hydrogen or a first-order substituent, preferably hydrogen,
R$_{23}$ and R$_{27}$ each signifies one of the heterocyclic second-order substituents of formulae (a), (b) or (c),
r signifies an integer from 1 to 3, preferably 1 or 2,
s signifies an integer from 1 to 3, preferably 1 or 2, and the total of r and s is 3 or 4.

Compounds of formula XVIII,

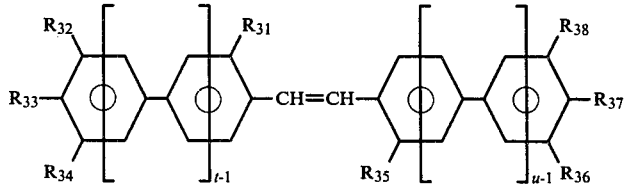

in which
R$_{31}$ and R$_{35}$ each signifies hydrogen, —CN or methyl, preferably —CN or methyl,
R$_{32}$, R$_{34}$, R$_{36}$ and R$_{38}$ each signifies hydrogen or a first-order substituent, preferably hydrogen,
one of the symbols R$_{33}$ and R$_{37}$ signifies one of the heterocycles (a), (b) or (c),
the other symbol R$_{33}$ or R$_{37}$ signifies hydrogen, a first-order substituent or a non-heterocyclic second-order substituent, t signifies an integer from 1 to 3, u signifies an integer from 1 to 3, the total of t and u is 3, 4 or 5, and where at least one of the substituents $R_{31}$, $R_{35}$ and $R_{33}$ or $R_{37}$ is a non-heterocyclic second-order substituent and, if the total of t and u is 3, at least two of the substituents $R_{31}$, $R_{35}$ and $R_{33}$ or $R_{37}$ are non-heterocyclic second-order substituents.

The essential feature of the compounds of formula I, above all with respect to their properties as optical brightening agents, is the combination between the basic structure and the second-order substituents and their position in the molecule. The compounds with generally the best properties are those in which one, two, three or all four of the substituents $R_1$, $R_3$, $R_5$ and $R_7$ are second-order substituents. The first-order substituents have no appreciable effect on the optical brightening properties, although they may, for example, affect the solubility in organic polymers. Even when second-order substituents are present in the molecule as substituents $R_2$, $R_4$, $R_6$ and $R_8$, they have no significant effect, compared with the second-order substituents $R_1$, $R_3$, $R_5$ and $R_7$, on the fluorescence of the brightener or consequently the fluorescence of the optically brightened substrate. Therefore, compounds of formula I in which $R_2$, $R_4$, $R_6$ and $R_8$ signify hydrogen are generally preferred to those in which $R_2$, $R_4$, $R_6$ and $R_8$ have a significance other than hydrogen.

The invention also provides a process for the production of compounds of formula I, which comprises (a) reacting a compound of formula II,

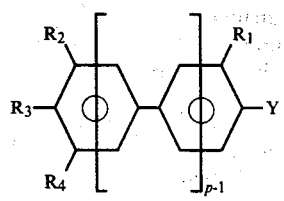

in which $R_1$ to $R_4$ and p are as defined above, and

Y signifies —CHO or a functional derivative thereof or —CO—COOH, with a compound of formula III,

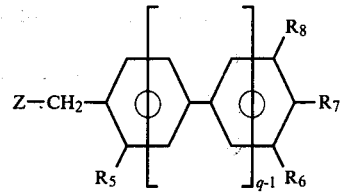

in which $R_5$ to $R_8$ and q are as defined above, and

Z signifies a substituent which activates the vicinal methylene group, or hydrogen if Y is an anile derivative of the aldehyde group and no equally active or more active methyl is present, and if a substituent Z with a significance other than hydrogen remains in the reaction product, replacing this with hydrogen, (b) cleavage of two of the substituents $Y_1$ and $Z_1$, with simultaneous reduction or oxidation if necessary, of compounds of formula IV,

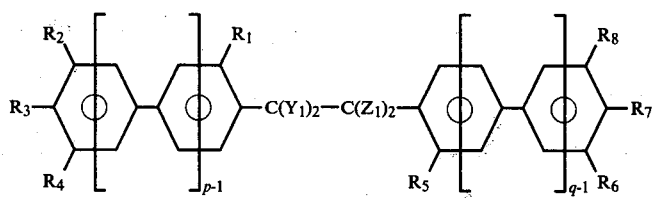

in which $R_1$ to $R_8$, p and q are as defined above, each $Y_1$ and each $Z_1$ independently signifies hydrogen, halogen, a hydroxyl or acyloxy group or $(Y_1)_2$ and/or $(Z_1)_2$ each signifies an oxo group, and if the substituents $Y_1$ and/or $Z_1$ have a significance other than hydrogen in the reaction product, replacement of such substituent by hydrogen, or (c) replacing a halogen atom in a compound of formula V,

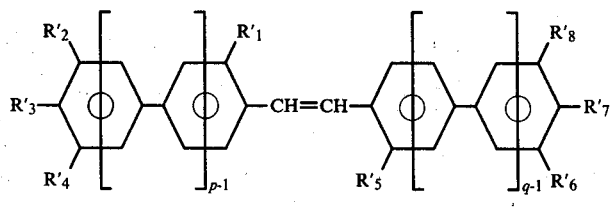

in which p and q are as defined above, and at least one of the symbols $R_1'$ to $R_8'$ signifies halogen and the remaining symbols have the same significance as $R_1$ to $R_8$ as defined above, to produce a corresponding compound of formula I in which at least one of $R_1$ to $R_8$ is nitrile, (d) converting a compound of formula I in which at least one of the substituents $R_2$, $R_3$, $R_4$, $R_6$, $R_7$ and $R_8$ signifies -CN by conversion of the -CN group into a compound of formula I having a corresponding carboxylic acid amide, carboxylic acid ester or free carboxylic acid group, (e) converting a compound of formula I in which at least one of the substituents $R_3$ and $R_7$ signifies a carboxylic acid, carboxylic acid ester or carboxylic acid amide group, into a compound of formula I having a corresponding heterocycle (a) substituent, if necessary after raction to the corresponding carboxylic acid halide group, (f) reacting in alkaline medium and/or under oxidative conditions, a compound of formula VI,

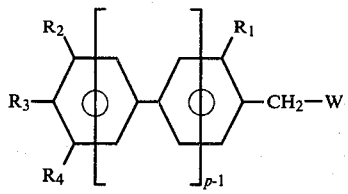

in which

R₁ to R₄ and p are as defined above, and

W signifies hydrogen, halogen or -P⊕(aryl)₃anion⊖, for which reaction the medium must be alkaline if W signifies halogen and must be carried out in the presence of an oxidizing agent if W signifies hydrogen and must be carried out in the presence of a proton acceptor and an oxidizing agent if W signifies [P(aryl)₃]⊕anion⊖, to form a compound of formula I in which R₅, R₆, R₇, R₈ and q are identical to R₁, R₂, R₃, R₄ and q in the compound of formula VI, or (g) by thermal treatment to split off CO₂ or N₂ groups in an inert gas atmosphere of compounds of formulae VII or VIII, respectively,

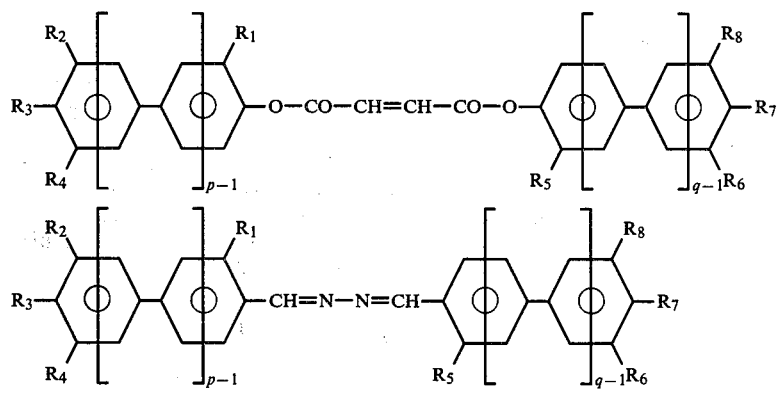

in which R₁ to R₈, p and q are as defined above, to split off the CO₂ or N₂ respectively.

Process variant (a) may be carried out in accordance with conventional methods, for example in the absence of air and preferably in the presence of a suitable catalyst, for example boric acid, zinc chloride, arylsulphonic acids, alkali metal and alkaline-earth salts of arylsulphonamides, acetic anhydride, alkali acetates, piperidine, alkali metal and alkaline-earth hydroxides, alkali metal and alkaline-earth alcoholates, suitably at temperatures of 0° to 200° C., preferably at 20° to 160° C.

In the compounds of formula II, Y signifies the group -CO-COOH or the group -CHO or a functional derivative of the aldehyde group suitable for the reaction, e.g. an anile, a hydrazone, an oxime or an azine. In the compounds of formula III, Z signifies hydrogen or a radical which activates the CH₂ group so that it can be reacted with the aldehyde or aldehyde derivative or with the ketocarboxylic acid group. Examples of such activating groups are the carboxyl group, a carboxylic acid ester or amide group, optionally the cyano group, and advantageously one of the groups

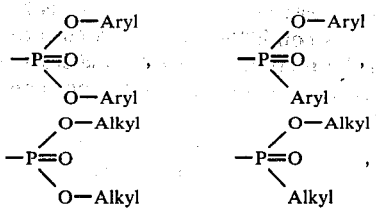

or -[P(aryl)₃]⊕anion⊖, where alkyl is preferably lower, e.g. with 1 to 6 carbon atoms, and is optionally substituted, e.g. by methoxy, ethoxy, phenyl or phenoxy, and includes cycloalkyl, e.g. cyclohexyl, and aryl is preferably mono-nuclear (optionally substituted phenyl) and anion⊖ is an equivalent of any suitable anion, preferably of a mineral acid, e.g. Cl⊖ or Br⊖.

The reaction can be carried out, for example, by melting the reactants, but it is preferred to use an inert organic solvent, e.g. aliphatic or aromatic, preferably halogenated, hydrocarbons, alcohols, ethers, glycols, formamide, dimethyl acetamide, N-methyl pyrrolidone, acetonitrile, dimethyl sulphoxide, tetramethylene sulphone or hexamethyl phosphoric triamide. For the reaction of compounds containing phosphorus (the Wittig and related reactions), see, e.g., "Organo-Phosphorus Compounds", International Symposium, Heidelberg 1964, Butterworths Scientific Publications. If a radical Z different from hydrogen is present in the reaction product, it is replaced by hydrogen by a suitable method in conventional manner.

Process variant (b) may be carried out in accordance with the conventional methods; for example compounds in which all the Y₁ and Z₁ radicals are hydrogen can be dehydrated to the corresponding stilbene compounds in analogy with the process described in the published German Patent Application 1,670,398, for example as described below. If one or more of the symbols Y₁ and Z₁ signifies halogen, preferably chlorine or bromine, and one or more of the remaining symbols Y₁ and Z₁ signify hydrogen, dehydrohalogenation may be carried out in known manner, preferably with heating, suitably at 100° to 300° C., or in particular 150° to 200° C., preferably in the presence of alcohols or glycols of high boiling point (ethylene glycol, propylene glycol) and/or strong bases (alkali, alcoholates); dehalogenation may be carried out in accordance with the known methods, for example with metals, e.g. zinc, or with copper (I) compounds or with triaryl phosphines in polar solvents, e.g. dimethyl formamide, dimethyl sulphoxide, N-methyl pyrrolidone etc., with heating, preferably at the refluxing temperature. With a dehydrohalogenation reaction, splitting off of acyl-OH may take place; acyl-OH signifies preferably a lower acid which splits off readily, e.g. benzoic acid or preferably acetic acid. Compounds in which two oxygen atoms are present in the bridge member —C(Y$_1$)$_2$—C(Z$_1$)$_2$—, optionally in addition to hydrogen, preferably benzoine compounds, can be reduced directly to the corresponding stilbene compounds, e.g. with zinc amalgam and an H$_2$/HCl current in boiling alcohol (cf. Baroni, C.A. 55, 1520e and J. Prakt. Chemie, 4th series, Vol. 20 (1963), pp. 56–61). Although this reaction is also suitable for the production of asymmetrical compounds, it is preferred to produce symmetrical compounds of formula I in this way, since, as is known, benzoine compounds, for example, can be produced from the corresponding aldehydes.

In process variant (c), the exchange of a halogen, preferably a bromine, atom by a nitrile group in the compounds of formula V may be carried out in known manner, for example by reaction in a suitable polar organic solvent, e.g. one of the aforenamed solvents, quinoline, quinaldine and/or alkylpyridines, e.g. lutidine, with a suitable cyanide, preferably CuCN, optionally in mixture with alkali or alkaline-earth cyanides.

In process variant (d), the conversion of a nitrile group into a corresponding carboxylic acid, carboxylic acid amide or carboxylic acid ester group is a conventional reaction and, for example, the acid group can be formed in the presence of water and/or alcohol and alkali or mineral acid with heating.

In process variant (e), the reaction of a carboxylic acid ester or halide group (R$_3$ and/or R$_7$) to an X-azole ring of formula (a) may be carried out in conventional manner, e.g. by reaction with a compound of formula XIX,

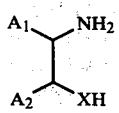   XIX where preferably A$_1$ and A$_2$ together form the atoms of an aromatic ring.

If the final product of formula I is to contain heterocyclic substituents R$_3$ and/or R$_7$, it is preferable to start from compounds which themselves contain such heterocycles.

In process variant (f), the reaction of compounds of formula VI may be carried out in accordance with conventional methods, for example as described in the following. If W signifies hydrogen, the reaction is carried out in the presence of an oxidizing agent, in particular oxygen or sulphur. If oxygen is used, the reaction can be carried out in analogy with the procedure described in the published German Patent Application 1,670,398 in a neutral to basic polar solvent, preferably a dialkylated acylamide, in particular dimethyl formamide, diethyl formamide, dimethyl acetamide or hexamethyl phosphoric acid triamide, in which case it is of advantage to work in the presence of a strongly basic alkali metal compound, preferably an alkali hydroxide, alcoholate or amide and, optionally, with oxygen in mixture with inert gases, e.g. in the form of air, and preferably at temperatures between 10° and 150° C., preferably between 30° and 100° C. When this procedure is employed it is necessary for the starting material of formula VI to be free from atoms replaceable by alkali metal. When sulphur is used as oxidizing agent, it is advantageous to react at temperatures between 250° and 350° C., preferably between 200° and 300° C., in the absence of solvents; the stoichiometric amount or an excess of sulphur can be used.

The reaction of the compounds of formula VI in which W signifies a halogen atom, preferably a chlorine or bromine atom, is carried out with strong bases, e.g. alkali and/or alkaline-earth hydroxide, alcoholate or amide, in particular potassium hydroxide, potassium tert. butylate or NaNH$_2$, in a polar solvent, for example dimethyl formamide, dimethyl acetamide, dimethyl sulphoxide, alcohol etc., with heating, for example between 60° and 200° C. depending on the solvent, preferably at the refluxing temperature.

A modification of the foregoing oxidation process with oxygen or sulphur consists in employing, in place of compounds of formula VI in which W signifies hydrogen, compounds in which W signifies -P⊕(aryl)$_3$anion⊖ where aryl is preferably mononuclear (optionally substituted phenyl) and anion⊖ has the aforesaid significance, and proceeding, e.g. in analogy with the process described in Chem. Ber. 103, 2995–2997 (1970). A further mode of operation consists in employing a compound of formula VI in which W signifies -P⊕(aryl)$_3$ anion⊖ and at least one of the anions has oxidizing properties and is used as oxidizing agent. Preferably periodates are used. The reaction can be carried out, for example, in analogy with the method described in the published German Patent Application 1,925,255 using anhydrous bases, in particular alkali metal or alkaline-earth alcoholates in dry alcohol, with heating, preferably at the refluxing temperature.

In process variant (g), the pyrolytic reactions of fumaric acid esters of formula VII and the aldazines of formulae VIII may be carried out in accordance with conventional methods, in particular under an inert gas atmosphere, optionally in the presence of a solvent of high boiling point, e.g. Dowtherm or solvent naphtha, and advantageously at temperatures between 200° and 400° C., preferably at about 250° C.

The intermediates of formula V can be produced by known methods, for example in analogy with the aforedescribed methods for the production of compounds of formula I, by the reaction of compounds of formula IX,

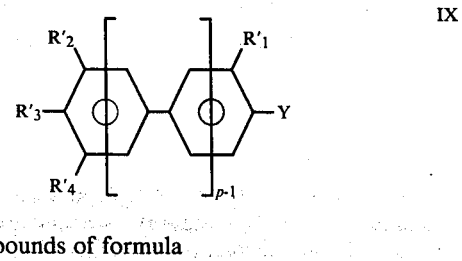

with compounds of formula

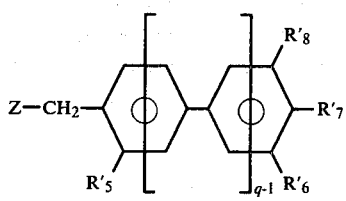 X in which
R$_1'$ to R$_8'$, p and q are as defined above,
in analogous manner to process (a) above, or by the reaction of compounds of formula XI,

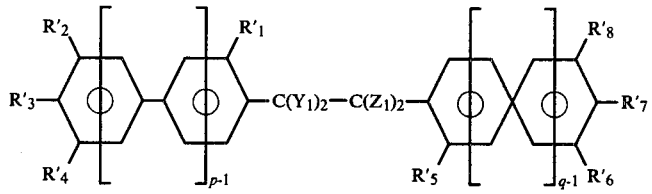 XI in which
R$_1'$ to R$_8'$, p, q, Y$_1$ and Z$_1$ are as defined above,
in analogous manner to process (b) above,
or (for symmetrical compounds of formula V) by the reaction of a compound of formula XII,

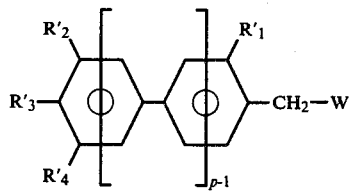 XII in which R$_1'$ to R$_4'$, p and W are as defined above, in analogous manner to process (f) above,
or by thermal treatment in analogous manner to process (g) above, of compounds of formula XIII or XIV,

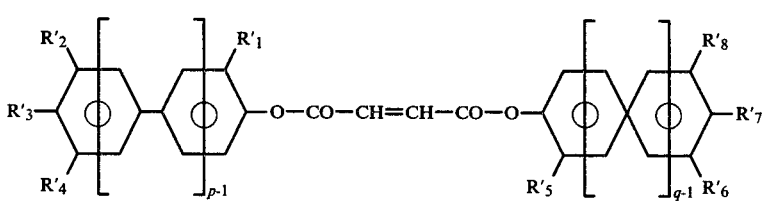 XIII

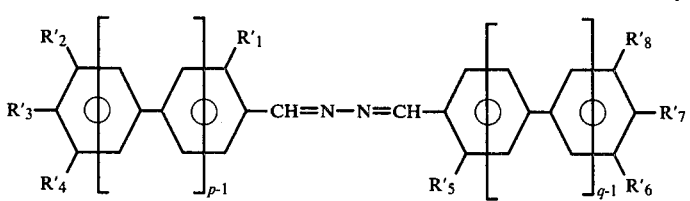 XIV in which R$_1'$ to R$_8'$, p and q are as defined above. Intermediates of formula V can also be produced by the reaction of compounds of formula XV,

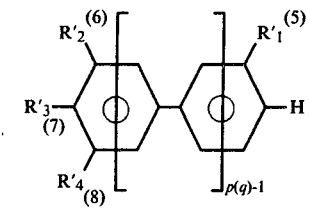 XV with a halogenacetaldehyde or a functional derivative thereof, with subsequent dehydrohalogenation and rearrangement of the reaction product. This reaction, preferably using compounds in which R$_3'$ is different from hydrogen, with halogenacetaldehyde, may be carried out in accordance with conventional methods, for example as given above for compounds of formula XI.

The compounds of formulae IV and XI in which at least one of the substituents Y$_1$ and Z$_1$ signifies halogen, preferably bromine, can be produced in analogy with the known methods, cf. for example J. Chem. Soc. 1943, 1-4.

The starting compounds of formulae II, III, VI, IX, X, XII and XV can be produced by known methods or in analogy with the known methods. The compounds of formulae IV, VII, VIII, XI, XIII and XIV can be produced in analogy with the known methods, e.g. by the reaction of hydrazine with the corresponding aldehydes to compounds of formula VIII or XIV, or by reaction of fumaric acid or a suitable derivative of this acid with the corresponding phenols to compounds of formula VII or XIII, or as given above for the compounds of formulae IV and XI.

The compounds of formula I produced as described above can be purified by precipitation from solution in an organic solvent, optionally with the addition of decolourizing carbon or bleaching earth. They have generally relatively little self-colour and are usually of low solubility in water. In organic solvents such as chlorobenzene, ortho-dichlorobenzene, dimethyl formamide, acetamide and 2-ethoxyethanol they dissolve with intense violet to blue fluorescence.

The compounds of formula I exhibit properties as optical brightening agents and are indicated for the optical brightening of a wide variety of textile and non-textile substrates, particularly of natural and synthetic organic polymers. Natural organic polymers include in particular fibres such as cotton, linen, wool and silk. Synthetic polymers, in particular fibre-forming polymers, are, for example, polyesters, polyamides, polyurethanes, polyolefins (polyethylene, polypropylene, modified polypropylene), polyvinyl acetate, polyvinyl chloride, polyvinylidene chloride, polyacrylonitrile, modified polyacrylonitrile, polystyrene, cellulose diacetate and cellulose triacetate.

The compounds of formula I can be applied as optical brighteners by any of the normal methods, for example in the form of solutions, as suspensions in organic solvents or as aqueous dispersions. They can be incorporated with good success in spinning melts and moulding materials, or in the monomers or prepolymers prior to the synthesis of the final polymer. The compounds of formula I are especially indicated for addition to polyester melts to brighten the spun filament. The amount of disclosed optical brightener used may vary from, e.g. 0.001 to 0.5% or preferably from 0.01 to 0.2% by weight relative to the substrate, depending on the method of application and the actual substrate. The compounds of formula I may be employed alone or in combination with other brighteners and in the presence of finishing agents, e.g. softeners, antistatic agents, surface-active agents, e.g. detergents, carriers and chemical bleaching agents.

In the following Examples, the parts and percentages, unless otherwise stated, are by weight; the parts by volume relate to the parts by weight as millilitres to grams. The temperatures are given in degrees centigrade. The melting points are uncorrected.

Example 1

Production of the compound of formula 1,

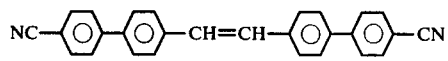

Method α

174.4 Parts of the compound of formula 2,

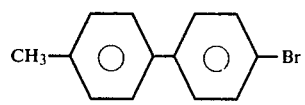

and 72.6 parts of copper (I) cyanide are added to 100 parts by volume of dimethyl formamide and reacted for 4 hours with stirring and reflux. The mixture is run with stirring into a solution of 283 parts of iron (III) chloride in 71 parts by volume of concentrated hydrochloric acid and 425 parts of water. Stirring is continued for 20 minutes at 60°–70°, then the suspension is cooled and the precipitate isolated by filtration with suction, washed with water and dried. After recrystallization from dilute methanol the compound of formula 3,

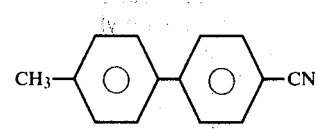

melting point 110°–111°, is obtained in good yield.

A mixture of 97.5 parts of the compound of formula 3, 90 parts of N-bromosuccinic imide and 1.1 parts of benzoyl peroxide in 505 parts by volume of carbon tetrachloride is reacted for 18 hours with stirring and reflux. The reaction mixture is cooled and the precipitate filtered with suction. The filtrate is strongly concentrated by evaporation under vacuum and cooled. The precipitated product is filtered with suction, washed with water and dried. On recrystallization from ligroin the compound of formula 4,

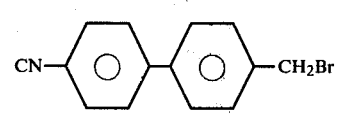

melting point 106°–107°, is obtained in very good yield.

82.1 Parts of the compound of formula 4 and 79.1 parts of triphenyl phosphine in 2000 parts by volume of toluene is boiled for 2 hours with stirring and reflux in the absence of moisture. After cooling, the precipitate is isolated by filtration with suction and dried. The compound of formula 5,

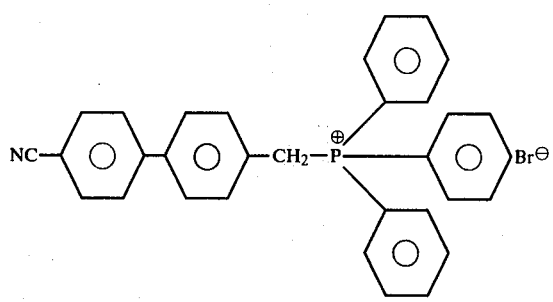

is obtained in almost quantitative yield and is reacted further without additional purification.

53.2 Parts of the compound of formula 5 are dissolved in 4000 parts of water with heating and stirring. A solution of 21.3 parts of sodium periodate in 200 parts of water is added rapidly and stirring continued for 10 minutes. After cooling, the precipitate is filtered with suction and dried. The compound of formula 6,

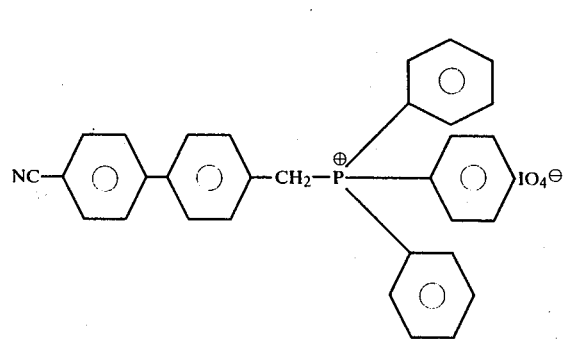

is obtained in very good yield.

To a mixture of 75 parts of the compound of formula 6 in 900 parts by volume of absolute ethyl alcohol, a solution of 9.8 parts of sodium ethylate in 290 parts by volume of absolute ethyl alcohol is slowly added at 60° with stirring. The mixture is held at the refluxing temperature for 3 hours, after which it is cooled and the precipitate filtered with suction, washed with water, dried and recrystallized from chlorobenzene with the addition of bleaching earth. The compound of formula 1, melting point 252°–255°, is obtained.

Method β

A clear solution of 26.7 parts of the phosphonium salt of formula 5 in 600 parts of dimethyl formamide is raised to 60°–65°. A freshly prepared solution of 1.5 parts of sodium in 30 parts of methyl alcohol is added in 15 minutes under nitrogen in the absence of moisture. The deep orange-red suspension is stirred for 30 minutes at 80° and then evaporated to dryness in a water-jet vacuum at 50°. The residue is stirred into 200 parts of xylene to give a suspension which is heated to 100°–110°. In the course of 2 hours a warm solution of 3.3 parts of sulphur in 130 parts of xylene is added dropwise. The suspension is stirred for 2 hours at 120°–125° until completely decolourized and then cooled. The precipitate is isolated by filtration with suction, washed with methyl alcohol and then with water, dried and recrystallized from trichlorobenzene with the addition of a small amount of bleaching earth. The compound of formula 1, melting point 253°–256°, is obtained in the form of pale yellow crystals.

Method γ

The compound of formula 1 is also obtainable by reacting a solution of 26.7 parts of the phosphonium salt of formula 5 in 600 parts of dry dimethyl formamide with 10.5 parts of 4-cyano-4'-biphenyl aldehyde in the presence of 3 parts of sodium methylate at 70°–80° under nitrogen.

The 4-cyano-4'-biphenyl aldehyde, melting point 157°–158°, can be obtained in high yield by the hydrolysis of the urotropine salt of 4-cyano-4'-(bromomethyl)-diphenyl [formula 4] in boiling aqueous acetic acid (the Sommelet reaction).

Method δ

Over about 30 minutes a solution of 27.2 parts of 4-(bromomethyl)-4'-cyanobiphenyl [formula 4] in 300 parts of dry xylene is added dropwise 20 parts of triethyl phosphite. On completion of the addition the xylene and the ethyl bromide formed in the reaction are distilled off in a column. The clear solution is held for 14 hours at 190°. After cooling to 60° the excess triethyl phosphite is removed in high vacuum at 0.01 mm. The crude diethyl phosphonate (31.2 parts) is set with 320 parts of dimethyl formamide and 21 parts of 4-cyano-4'-diphenyl aldehyde under nitrogen in the absence of moisture and raised to about 40°. A clear solution forms, into which a freshly prepared solution of 2.6 parts of sodium in 30 parts of methyl alcohol is dropped in 15 minutes. On completion of the addition the brown-yellow suspension is stirred further for 30 minutes at 40° and then for 3 hours at 80°. After cooling the reaction mixture is diluted with 640 parts of methyl alcohol and the precipitate is filtered with suction, washed with water, dried and recrystallized from dimethyl formamide or trichlorobenzene. The compound of formula 1 is obtained in analytically pure state. It melts at 253°–256°.

Method ε

A mixture of 24.5 parts of p,p'-bis-(4-bromophenyl)-stilbene and 13.4 parts of copper (I) cyanide in 200 parts by volume of quinoline is reacted for 16 hours with reflux. After cooling a dark brown slurry is obtained, which is filtered with suction. The filter cake is treated successively with about 100 parts by volume each of cold concentrated hydrochloric acid, water, concentrated ammonia, water and finally acetone, after which it is dried. A pale brown powder is obtained which is dissolved in 2000 parts by volume of 1,2,4-trichlorobenzene, with the subsequent addition of a few parts of bleaching earth. The mixture is boiled for 10 to 20 minutes with reflux and filtered hot. The hot solution can be clarified further by boiling for a short time with a few parts by weight of basic aluminum oxide, activity stage II, followed by hot filtration. After cooling the precipitated substance is isolated by filtration with suction in the form of long spear-shaped, pale yellow needles, washed with cold methanol and vacuum dried. Approximately 16 parts by weight (80% of theory) of the crude product are obtained. After further recrystallization (twice from trichlorobenzene or dimethyl formamide) a pale yellow compound conforming to formula 1, melting point 252°–255°, is obtained in good yield. The solution of this compound in 1,2,4-trichlorobenzene is colourless, fluoresces intensely with a violet colour and in ultra-violet radiation has its absorption maximum wavelength at 360–363 nm (extinction: $6.10^4$).

The p,p'-bis-(4-bromophenyl)-stilbene of formula 7,

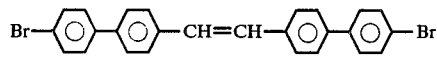

used as starting material can be produced, for example, by the following methods.

In the absence of moisture and atmospheric oxygen, 13.1 parts of triphenyl phosphine are added at 60°–65° to a solution of 16.3 parts of 4-bromo-4'-(bromomethyl)-biphenyl in 400 parts of dimethyl formamide. Stirring is continued for 3 hours at 80°, then the clear, colourless solution is adjusted to 60° again and in 15 minutes a freshly prepared solution of 1.3 parts of sodium in 25 parts of methyl alcohol is added dropwise. The deep orange-red suspension is stirred for a further 30 minutes and then evaporated to dryness in a water-jet vacuum at 50°. The residue is stirred into 200 parts of xylene, the suspension raised to 100°–110° and a warm solution of 3.3 parts of sulphur in 130 parts of xylene added dropwise in 2 hours. Stirring is continued for 2 hours at 120°–125° for complete decolourization. After cooling to room temperature the yellow precipitate is filtered with suction, washed with methyl alcohol and water and dried. The compound of formula 7 is obtained in good yield with melting point 346°–352° and is sufficiently pure for further reaction. It can be purified by recrystallization from 1,2,4-trichlorobenzene with the addition of a small amount of bleaching earth, on which it is obtained in the form of pale yellow needles with melting point 356°–358°.

The 4-bromo-4'-(bromomethyl)-biphenyl, melting point 92°–94°, can be produced, for example, by side-chain bromination of 4-bromo-4'-methyl biphenyl [formula 2] in chlorobenzene with ultra-violet irradiation.

The solution of the phosphonium salt in 400 parts of dimethyl formamide obtained from 16.3 parts of 4-bromo-4'-(bromomethyl)-biphenyl and 13.1 parts of triphenyl phosphine (see above), when reacted with 13.1 parts of 4-bromo-4'-biphenylaldehyde in the presence of 3 parts of sodium methylate at 70°–80°, also gives the compound of formula 7 in good yield in the form of a pale yellow powder with melting point 348°–356°.

The 4-bromo-4'-diphenylaldehyde, melting point 137°–140°, can be produced in a simple manner by hydrolysis of the urotropine salt of 4-bromo-4'-(bromomethyl)-biphenyl in boiling aqueous acetic acid solution (the Sommelet reaction).

Treatment of a 20% solution of the fumaric acid bis-(4'-bromodiphenyl-4-)ester of formula 8,

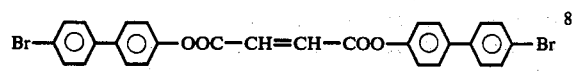

in boiling Dowtherm A (a mixture of approximately 78% diphenyl ether and 22% diphenyl) for 50 hours under nitrogen, purification of the cold filtered crude product by treatment with a little boiling dimethyl formamide for a short time and recrystallization of the hot filtered residue from 1,2,4-trichlorobenzene using some bleaching earth results in the compound of formula 7 in the form of pale yellow crystals. It is analytically pure and melts at 356°–358°.

The fumaric acid diaryl ester of formula 8 can be effectively produced by treating a solution of 2 mols of 4'-bromo-4-hydroxy-diphenyl (lit. melting point 164°–166°) and 1 mol of fumaric acid dichloride in o-dichlorobenzene for 2 hours at 150° and for a further 4 hours at the refluxing temperature, cooling, isolation by filtration with suction and recrystallization from chlorobenzene using bleaching earth. Yellow needles, melting point 256°–259°, are obtained, which are sufficiently pure for further reaction.

The stilbene compound of formula 7 can be produced from 2 mols of 4'-bromodiphenyl aldehyde-4 by benzoine condensation, subsequent reduction to the corresponding desoxybenzoine with simultaneous thermal treatment with aluminium isopropylate according to G. Drefahl and K. Thalmann, J. prakt. Chemie, 4th series, 20, 60 (1963), by using in place of p-terphenyl aldehyde-4 the equivalent amount of 4'-bromo-diphenyl aldehyde-4, on which intermediates of the following formulae are obtained,

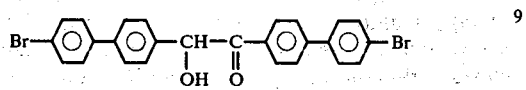

and

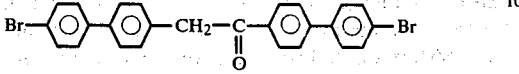

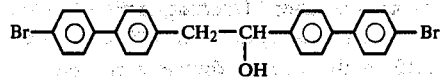

or by reaction of 2 mols of 4'-bromodiphenyl aldehyde-4 with 1 mol of hydrazine to the aldazine of formula,

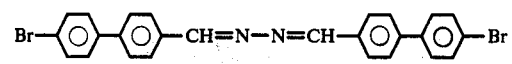

and thermal treatment of this compound in Dowtherm A under the same reaction conditions as in the thermal treatment of the fumaric acid ester of formula 8, (cf. Bull. Soc. Chim. France 1970, 2, pp. 525–527), or by cleavage of hydrogen bromide, with simultaneous rearrangement, from the compound of formula 13,

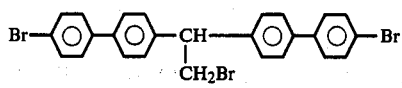

in boiling ethylene glycol [H. Sieber, Liebigs Ann. Chem. 730, 31–46, 1969] or in amyl alcohol [Al-Attar and R. Wizinger, Helv. Chim. Acta 46, 1286, 1963; the 1,1-diaryl-2-bromomethane of formula 13 is accessible from 4-bromodiphenyl and bromacetaldehyde]; or by dehalogenation of the compound of formula 14,

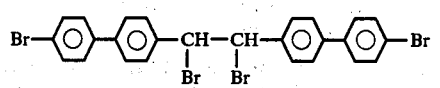

with reducing metals, e.g. zinc, or copper (I) compounds (Soc. 1943, 1:, Referat C. 1943 II, 715) or triphenyl phosphine (J. Org. Chem. 36, 2377–79, 1971).

If the compound of formula 14 is reacted with excess copper (I) cyanide under suitable conditions, the two bromine atoms bound to the benzene nuclei are removed and replaced by cyano groups. The compound of formula (1) is then obtained directly (method ε bis).

Method θ

23.5 Parts by weight of fumaric acid bis-(4'-cyanodiphenyl-4)-ester of formula 15,

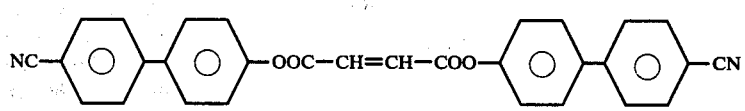

are dissolved in 70 parts by volume of Dowtherm A (a mixture of about 78% diphenyl ether and about 22% diphenyl) with heating. The solution is reacted for 50 hours at about 250° under nitrogen with reflux. After cooling the crystallized crude product is recrystallized in the same way as in method α. The compound obtained has the formula 1 and shows the properties given in method (a).

The fumaric acid ester of formula 15 is produced analogously to the reaction of 4'-bromo-4-hydroxydiphenyl to the fumaric acid ester of formula 8 from 4'-cyano-4-hydroxydiphenyl (production from the bromine derivative by reaction with CuCN in dimethyl formamide) and fumaric acid chloride with recrystallization from benzene using bleaching earth. A powder of beige colour, melting point 260°–270°, is obtained which is sufficiently pure for further reaction.

EXAMPLE 2

Production of the compound of formula 16,

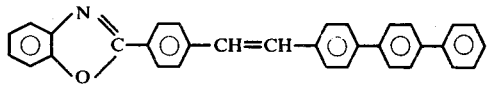

18.9 Parts of the compound of formula 17,

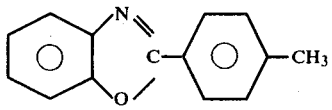

30 parts of p-terphenyl aldehyde anile and 20.1 parts of potassium tert. butylate are entered into 960 parts by volume of dimethyl formamide. The solution is raised to 90° in 30 minutes under a nitrogen atmosphere with stirring and held at 90°–95° for 1 hour with continued stirring. After cooling the reaction mixture to 10°–20°, 630 parts of water and then 540 parts by volume of 10% hydrochloric acid are added. The precipitate is filtered with suction, washed with water and dried. After recrystallization from o-dichlorobenzene with the addition of bleaching earth the compound of formula 16, melting point > 350°, is obtained in good yield. It fluoresces blue-violet in trichlorobenzene solution and the absorption maximum wavelength in this solvent is at 375 nm.

EXAMPLE 3

If the procedure of Example 2 is carried out using, in place of 18.9 parts of the compound of formula 17, 24 parts of the compound of formula 18,

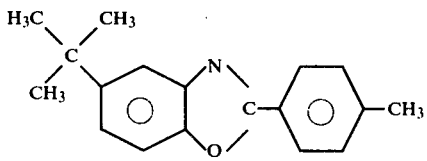

the compound of formula 19,

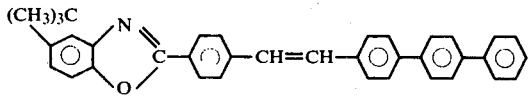

is obtained in good yield. On purification from dimethyl formamide it is obtained as a pale yellow powder with melting point 133° and absorption maximum wavelength at 379 nm in trichlorobenzene solution.

EXAMPLE 4

Production of the compound of formula 20,

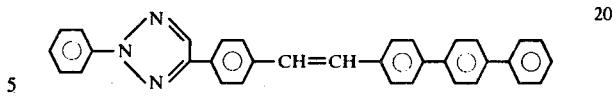

31.4 Parts of the compound of formula 21,

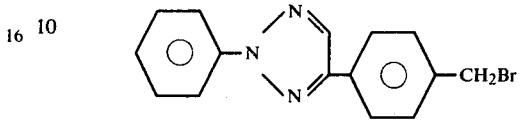

and 28 parts of triphenyl phosphine are added to 500 parts by volume of dimethyl formamide and reacted for 3 hours at 80° with sti-ring. After this time 26 parts of p-terphenyl aldehyde are added to the clear solution, followed by 11 parts of sodium methylate. The mixture is stirred further for 3 hours at 80° and then cooled to 10°–20°. The precipitate is filtered with suction, dried and recrystallized from chlorobenzene with the addition of bleaching earth. The compound of formula 20 is obtained in good yield with melting point 320° and an absorption maximum wavelength in trichlorobenzene at 363 nm.

The compound of formula 21 can be produced as follows.

11.3 Parts of sodium are dissolved in 200 parts of absolute ethyl alcohol with stirring. At room temperature 57.2 parts of iso-amyl nitrite are slowly added. The mixture is cooled to 0°–5° and at this temperature 65.7 parts of 4-methyl acetophenone are gradually added dropwise. The mixture is stirred for 24 hours at 0°–5° and then for a further 24 hours at room temperature. The precipitate is isolated by filtration with suction, washed thoroughly with ether and dried. It is dissolved in 800 parts of ice-water, the solution decolourized with activated carbon and then set slowly with 80 parts of glacial acetic acid with vigorous stirring. A white precipitate forms which is filtered with suction, washed until neutral and dried. The compound of formula 22,

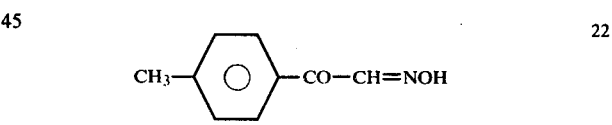

melting point 108°–109°, is obtained in good yield and is reacted further without additional purification.

20.8 Parts of the compound of formula 22 are dissolved in 185 parts of methanol and a solution of 2.7 parts of glacial acetic acid in 2.7 parts of water is added to the solution. 13.7 Parts of phenyl hydrazine are slowly added dropwise and stirring continued for a further hour. The reaction mixture is fully evaporated in vacuum and the dry crude product suspended in 116 parts of glacial acetic acid. The suspension is gradually added to 250 parts of melted urea at 150° with stirring. Stirring is continued for 3 hours at 175°, then the mixture is cooled to 140° and 400 parts of 2 N sodium hydroxide solution are gradually added. The reaction mixture is finally cooled to 0°–5° and the precipitate filtered with suction, washed neutral with water and dried. After crystallization from petroleum ether the compound of formula 23,

[Structure 23: phenyl-N-N=CH-pyrazole-type with tolyl-CH3]

is obtained with melting point 66°–68°.

A solution of 20 parts of the compound of formula 23, 15.2 parts of N-bromosuccinimide and 0.2 parts of benzoyl peroxide in 85 parts by volume of carbon tetrachloride is reacted for 6 hours with stirring and reflux. After cooling the precipitate is filtered with suction and the filtrate heavily evaporated with vacuum, on which the compound of formula 21 settles out. On purification from ligroin it has a melting point of 121°–122°. The crude product is however sufficiently pure for the next reaction.

EXAMPLE 5

Production of the compound of formula 24,

[Structure 24]

If the procedure of Example 4 is carried out using in place of 31.4 parts of the compound of formula 21, 35.3 parts of the compound of formula 25,

[Structure 25]

the compound of formula 24 is obtained in good yield. After purification from dimethyl formamide with the aid of decolourizing carbon its melting point is 267°–268° and the absorption maximum wavelength in trichlorobenzene at 370 nm.

The compound of formula 25 can be produced as follows. 100 Parts of 3-cyano-4-methyl-1-aminobenzene (prepared from the corresponding nitro compound by reduction according to Bechamp) are dissolved in 320 parts by volume of glacial acetic acid. The solution is dropped into a mixture of 42 parts by volume of sulphuric acid and 610 parts of ice in 30 minutes, after which a solution of 54 parts of sodium nitrite in 114 parts of water is added dropwise. The resulting diazo solution is stirred for a further 30 minutes.

A solution of 9.9 parts of sodium sulphite in 76 parts of water is added to 70 parts of isonitrosoacetone in 760 parts of water, followed by a solution of 19 parts of copper sulphate in 76 parts of water. After cooling to 0° the diazo solution is added. The mixture is allowed to stand for 12 hours, after which the precipitate is filtered with sucton, washed with water and dried. On recrystallization from ligroin the compound of formula 26,

[Structure 26]

melting point 185°–186°, is obtained in good yield.

A hot solution of 71.3 parts of the compound of formula 26 in 1060 parts by volume of methanol is set with 151.2 parts by volume of acetic acid 1:1. The mixture is held at the boil for a short time, then 38.1 parts of phenyl hydrazine are added slowly. The suspension is boiled for a further 2 hours with reflux and cooled, and the precipitate filtered with suction and dried. The compound of formula 27,

[Structure 27]

melting point 248° (crystallization from chlorobenzene), is obtained in very good yield.

300 Parts by volume of acetic anhydride and 200 parts by volume of pyridine are added to 73 parts of the compound of formula 27 in 275 parts by volume of dimethyl formamide. The mixture is raised to 80° in 1 hour 30 minutes, held at this temperature for 2 hours and then at 100° for 4 hours, after which it is raised to the boiling temperature and boiled for 30 minutes with reflux. After cooling the reaction mixture is run into 2000 parts of water, the precipitate filtered with suction, dried and recrystallized from methanol. The compound of formula 28,

[Structure 28]

melting point 141°–142°, is obtained in very good yield.

The compound of formula 28 is reacted further with N-bromosuccinimide to the compound of formula 25 in analogy with the method given for the compound of formula 23. On purification from ligroin the compound of formula 25 has a melting point of 147°–148°.

EXAMPLE 6

Production of the compound of formula 29,

[Structure 29]

20 Parts of the compound of formula 30,

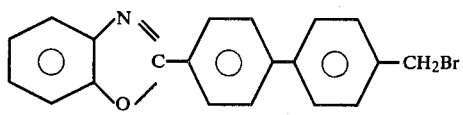

and 15.3 parts of triphenyl phosphine are dissolved in 480 parts by volume of dimethyl formamide. The solution is held for 3 hours at 80° under a nitrogen atmosphere with stirring. The clear solution is then set with 12.4 parts of the compound of formula 31,

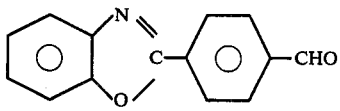

and 6 parts of sodium methylate, and then heated further for 4 hours at 80°. After cooling the precipitate is filtered with suction, washed with water and dried. On recrystallization from chlorobenzene with the addition of bleaching earth, the compound of formula 29 is obtained in good yield. Its melting point is above 350° and the absorption maximum wavelength in dimethyl sulphoxide is at 375 nm.

The compound of formula 30 can be formed from the compound of formula 32,

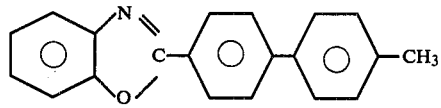

by bromination with N-bromosuccinimide in analogy with the method given for the compound of formula 23. On recrystallization from chlorobenzene its melting point is 195°–197°.

The compound of formula 32 can be produced as follows.

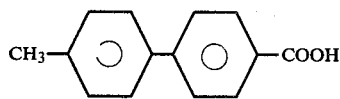

and 19.4 parts of o-aminophenol in solution in 284 parts of polyphosphoric acid are raised to 110° with stirring under a nitrogen atmosphere, held at this temperature for 10 minutes, then heated further to 210° and stirred for 3 hours at 210°–220°. The temperature is allowed to fall to about 100° and the mixture unloaded into 1400 parts of ice-water. The precipitate is filtered with suction, washed with 10% soda solution and then with water until neutral, and dried. The compound of formula 32 is obtained in almost quantitative yield and is used further without additional purification. After recrystallization from ethanol the melting point of the compound of formula 32 is 169°–170°.

The compound of formula 31 can be produced as follows. A mixture of 20 parts of the compound of formula

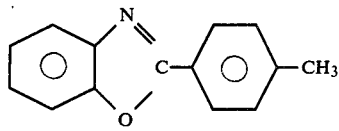

in 500 parts of chlorobenzene is raised to the boiling temperature with stirring and set slowly, with simultaneous ultra-violet irradiation, with a solution of 15.3 parts of bromine in 100 parts of chlorobenzene. Stirring and irradiation are continued at boiling temperature until the evolution of hydrogen bromide abates (5–6 hours). The mixture is cooled and the precipitate filtered with suction, washed with cold chlorobenzene and dried. The compound of formula 35,

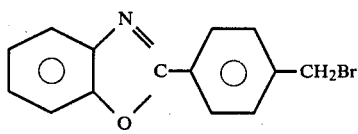

is obtained in very good yield. On purification from chlorobenzene its melting point is 168°–169°.

The compound of formula 31 is finally obtained from the compound of formula 35 by the Sommelet reaction; its melting point is 160°–161°.

EXAMPLE 7

Production of the compound of formula 36,

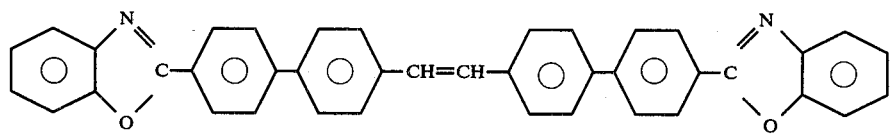

In analogy with the procedure of Example 1, the compound of formula 30 is converted by reaction with triphenyl phosphine and exchange of the bromine anion for the periodate anion into the compound of formula 37,

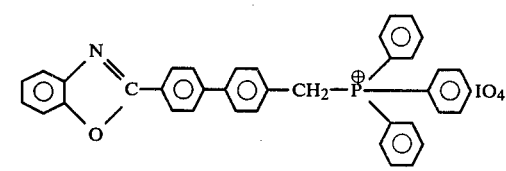

which is reacted with sodium ethylate to yield the compound of formula 36. On purification from dimethyo formamide, the compound of formula 36 has a melting point above 350°; the absorption maximum wavelength in trichlorobenzene solution is at 372 nm.

EXAMPLE 8

Production of the compound of formula 38,

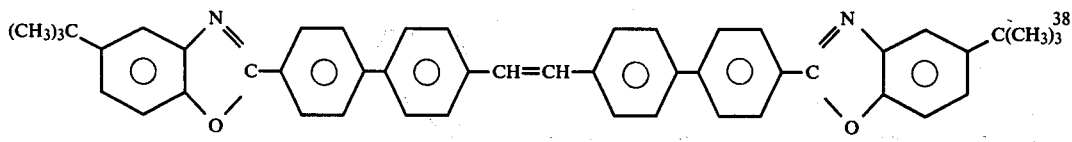

In analogy with the procedures of Examples 1 and 7, from the compound of formula 39,

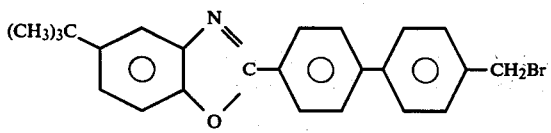

is produced the compound of formula 38; its melting point is above 350° and the absorption maximum wavelength in trichlorobenzene is at 375 nm.

EXAMPLE 9

In analogy with the operating procedures of Examples 1 and 7 the compound of formula 41,

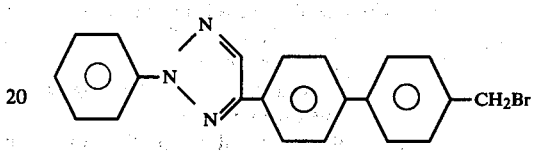

is reacted to yield the compound of formula 42,

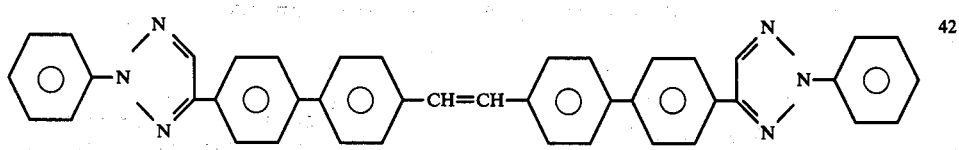

The compound of formula 39 can be obtained from the compound of formula 40,

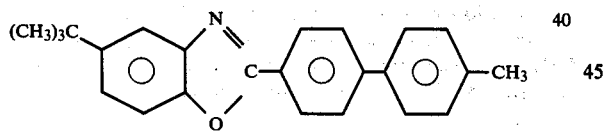

in analogy with the method given for the compound of formula 23. After recrystallization from ethanol its melting point is 205°–206°. The compound of formula 40 can be produced as follows.

A mixture of 16.5 parts of 2-hydroxy-5-tert.butyl-1-aminobenzene, 21.2 parts of the compound of formula 33, 2 parts of boric acid and 8.5 parts of piperidine in 140 parts by volume of 1,2,4-trichlorobenzene is raised to 160° in 1 hour with stirring under a nitrogen atmosphere, held at 160°–170° for 1 hour and then heated further to 200° in 1 hour. The mixture is stirred at 210° for 1 hour and finally held at boiling temperature for 4 hours with reflux. The water formed in the reaction is azeotropically removed. After cooling, 70 parts by volume of isopropyl alcohol are added to the reaction mixture. Stirring is continued for 30 minutes, then the precipitate is filtered with suction and dried. It is recrystallized from ethanol, on which the compound of formula 40 is obtained in very good yield with melting point 167°–168°.

The compound of formula 41 can be formed from the starting compound of formula 43,

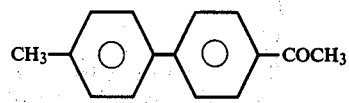

in accordance with the mode of operation given for the compounds of formulae 22, 23 and 21.

EXAMPLE 10

In analogy with the procedures described in Examples 1 and 7 the compound of formula 44,

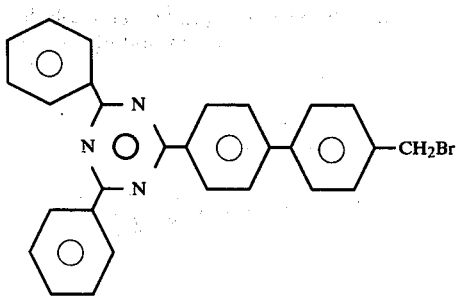

(melting point 223°) is employed to yield the compound of formula 45,

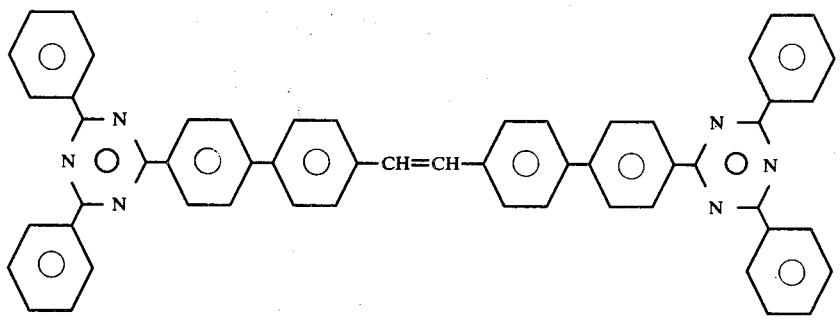

the melting point of which is above 360° and the absorption maximum wavelength in CHCl₃ at 382 nm. The compound of formula 44 can be produced by bromination of the corresponding methyl compound (melting point 215°–216°), which in its turn can be obtained from the compound of formula 33 in analogy with the method described in Helv. Chim. Acta 50, 955 (1967).

maximum wavelength in CHCl₃ is at 360 nm, the emission maximum in CHCl₃ at 433 nm.

EXAMPLE 13

If the procedure of Example 1, method θ is adopted, with the 23.5 parts of fumaric acid bis-(4'-cyanodiphenyl-4)-ester of formula 15 replaced by 28.2 parts of the fumaric acid ester of formula 48,

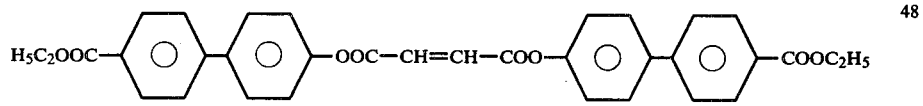

EXAMPLE 11

In analogy with the procedure of Example 5, the compound of formula 46,

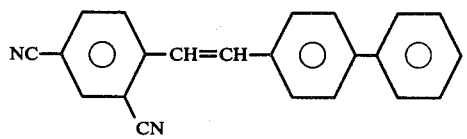

(melting point 300°–302°) can be produced from 2,4-dicyanobenzyl bromide and diphenyl aldehyde. The 2,4-dicyanobenzyl bromide (melting point 106°) can be obtained by bromination of 2,4-dicyanotoluene (melting point 142°–143°) with bromine in chlorobenzene with ultra-violet irradiation. The 2,4-dicyanotoluene can be formed from 3-cyano-4-methyl-1-aminobenzene by the Sandmeyer reaction.

EXAMPLE 12

In full analogy with the operating procedure yielding the compound of formula 24, the compound of formula 47,

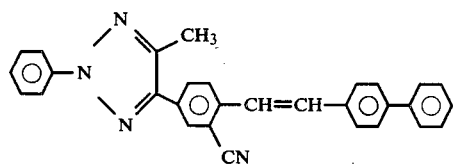

is produced from the compound of formula 25 and diphenyl aldehyde. On recrystallization from "Cellosolve" its melting point is 245°–246°. The absorption after repeated recrystallization from 1,2,4-trichlorobenzene with the addition of bleaching earth, a yellow-green powder is obtained which did not melt at 350°.

This compound, which is obtained in the analytically pure state, agrees with the formula 49, $$H_5C_2OOC-\bigcirc-\bigcirc-CH=CH-\bigcirc-\bigcirc-COOC_2H_5 \quad 49$$

The solution of this compound in 1,2,4-trichlorobenzene is colourless, shows intense red-violet fluorescence and has its absorption maximum wavelength in ultra-violet radiation at 361 nm (extinction maximum $5.6 \times 10^4$).

The fumaric acid ester of formula 48 can be derived from 4'-hydroxydiphenyl-4-carboxylic acid ethylester (accessible from 4'-cyano-4-hydroxydiphenyl by alcoholysis with ethyl alcohol and sulphuric acid) and fumaric acid dichloride in the same way as the fumaric acid esters of formulae 8 and 15. Subsequent purification by recrystallization from chlorobenzene with the aid of bleaching earth results in a yellow crystalline powder which melts at 259°–267° and is sufficiently pure for further use.

EXAMPLE 14

In analogy with the procedure of Example 1, the compound of formula 50,

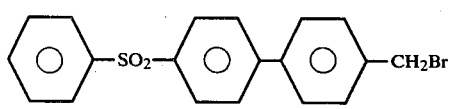

is reacted to yield the compound of formula 51,

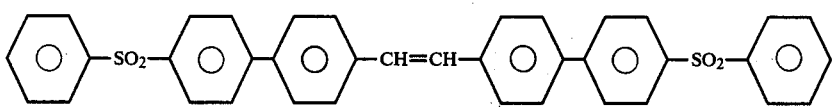

The compound of formula 50 can be produced by bromination of the corresponding methyl compound of formula 52,

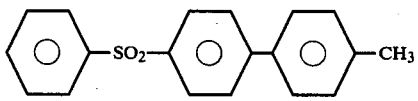

which in turn can be obtained from methyl-1,1'-diphenyl-4'-sulphonic acid (obtainable in accordance with Ber. 65, (1932), pp. 1382–87) in analogy with the method given in J. Chem. Soc. London 1960, II, p. 2508. Solutions of the compound of formula 51 in o-dichlorobenzene display intense blue-violet fluorescence.

EXAMPLE 15

In analogy with the procedure of Example 5, the compound of formula 25 and an equivalent amount of the compound of formula 53,

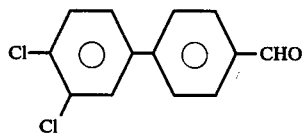

can be employed as starting materials to yield the compound of formula 54,

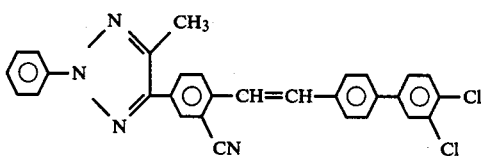

In chlorobenzene solution the latter compound fluoresces blue-violet. The compound of formula 53 can be obtained, for example, by working in accordance with the teaching of U.S. Pat. No. 2,280,504 (cf. Belstein E. III 7³, 2091).

EXAMPLE 16

If the procedure of Example 1, method ε is employed with the 24.5 parts of the compound of formula 7 replaced by 26 parts of the compound of formula 55,

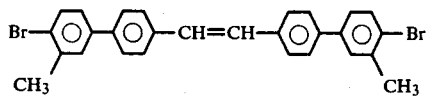

a pale yellow compound with the formula 56,

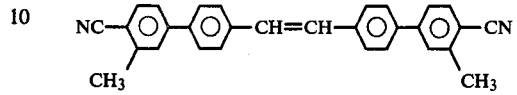

is obtained, which shows violet fluorescence in trichlorobenzene solution.

The compound of formula 55 can be obtained, for example, by reaction of the compound of formula 57,

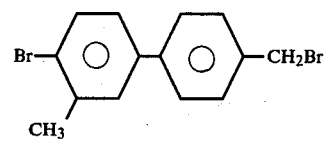

with the stoichiometric amount of triphenyl phosphine, with simultaneous exchange of the bromine anion by the periodate anion, to give the compound of formula 58,

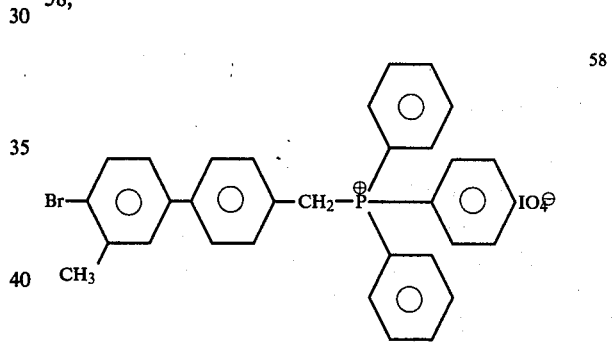

which is reacted with sodium ethylate in analogy with Example 7. The starting compound of formula 57 is formed by reacting 3-methyl-4-bromodiphenyl (Bp₇₆₀ 318°–323°; Bp.₃ 165°–170°; $n_D^{25}$=1,6150; literature: Beilstein E III, Vol. V, p. 1800; J. Am. Chem. Soc. 55 (1933), 1212–1217 and 58 (1936), 1249) with excess paraformaldehyde and excess sodium bromide for 30 hours in a sulphuric acidglacial acetic acid mixture at 100°, with subsequent working up by normal methods, on which it is obtained in good yield.

APPLICATION EXAMPLE A

Two parts of the compound of formula 1 are mixed with 2 parts of a highly sulphonated castor oil, 8 parts of sodium dioctyl phenyl polyglycol ether oxyacetate containing 40 ethenoxy groups in the molecule, and 80 parts of water. The mixture is comminuted in a suitable machine, for example a sand mill, until the predominant particle size fraction is of the order of 0.5 to 2 microns.

A bath is prepared with 3000 parts of water, 15 parts of a commercial carrier, e.g. ortho-dichlorobenzene, and 2 parts of the mixture as above. At 50° 100 parts of a fabric of polyester (polyethylene terephthalate) fibre are entered into the bath. The bath is brought to the boil in 30 minutes and the fabric treated for 45 minutes at the boil with reflux. On removal the fabric is treated for 10 minutes at 70° and liquor to goods ratio 40:1 in an aqueous solution containing 1.5 g/l octyl phenyl decaglycolether, with subsequent rinsing and drying. The treated polyester fabric shows a pronounced optical white effect. If the treatment is carried out in an enclosed machine at 120°–130°, comparable white effects are obtained without the addition of a carrier.

APPLICATION EXAMPLE B

A blend fabric of cotton and a polyester fibre, e.g. polyethylene terephthalate, is padded at room temperature with a dispersion of 20 parts of the brightener mixture formed as in Example A in 1000 parts of water. The padding expression leaves the fabric containing 80% of its weight of the dispersion. After intermediate drying for 30 minutes at 60° the fabric is dry heat treated for 1 minute at 200° for fixation. The whiteness value obtained is close to that given by the method of application described in the preceding Application Example. If a fabric of polyester fibre alone is treated ("Dacron", "Terylene", "Diolen" etc.), similar white effects are obtained.

APPLICATION EXAMPLE C

100 Parts of a fabric of polyester fibre, e.g. polyethylene terephthalate, are treated for 1 hour 30 minutes at 90°–95° in a bath consisting of 3000 parts of water, 6 parts of 85% formic acid, 6 parts of 80% sodium chlorite, 5 parts of a carrier, e.g. a trichlorobenzene mixture, and 2 parts of the brightener mixture prepared as given in Application Example A. On removal from the bath the fabric is washed off, rinsed and dried. It shows a higher whiteness value than a comparable fabric which has been bleached under the same conditions but without the addition of the compound of formula 1.

APPLICATION EXAMPLE D

50 Parts of a polyester fabric are entered into a mixture of 250 parts by volume of trichloroethylene and 250 parts by volume of chlorobenzene containing in solution 0.2 parts of the compound of formula 1 and treated for a short time with constant agitation. The excess solvent is removed by centrifuging to leave the fabric containing roughly its own weight of the application solution. After vacuum drying a 60°, the fabric is treated for 15 minutes in water vapour at 120° to 130°. The fabric has an appreciably whiter appearance than a comparable polyester fabric which has been treated under the same conditions but without a brightener addition.

If in place of polyester fabric a blend fabric of cotton and a polyester fibre, e.g. "Diolen", is treated by this method, a white effect of similar quality is obtained.

APPLICATION EXAMPLE E

In the feed vessel of a melt spinning machine 200 parts of polyethylene terephthalate are melted at 280° under nitrogen. 0.04 Parts of the compound of formula 1 are metered into the melt with stirring. The brightener melt at this temperature and is homogeneously distributed in the polyester as stirring continues. It is followed by 4 parts of titanium dioxide as delustrant, with further stirring for homogenization. The melt is extruded through a spinning nozzle and the filament formed is cooled by a water jet or by air, cold drawn and wound on bobbins.

Products made of the filament have a considerably higher whiteness value than comparable products of spun filament containing no incorporated brightener.

A comparable white effect is obtained when the compound of formula 45 is used in place of the compound of formula 1.

APPLICATION EXAMPLE F

A mixture of 1000 parts of dimethyl terephthalate, 665 parts of ethylene glycol, 0.55 parts of manganese acetate, 0.18 parts of antimony trioxide and 0.3 parts of the compound of formula 1 is heated in a reaction vessel of stainless steel fitted with a stirrer and a descending cooler. Splitting off of the methanol begins at about 160° and takes 2 hours 30 minutes to complete. Towards the end of this period the temperature increases to about 225°. Four parts of titanium dioxide and 0.3 parts of phosphoric acid are added to the melt, the pressure in the reaction vessel is reduced to below 1 mm and the temperature maintained at 290° until the desired degree of polymerization is reached. The polymer thus produced is extruded in conventional manner at 2–5 atmospheres excess pressure (inert gas) in the form of filament. The polyester filament has a high degree of whiteness which is fast to light and washing.

APPLICATION EXAMPLE G

500 Parts of polyamide 6 chips, 1.5 parts of titanium dioxide and 0.1 part of the compound of formula 20 are intimately mixed in a mixer and the mixture charged into the feed vessel of a melt spinning machine, where it is melted at 250°–260° in the absence of oxygen. The melt is extruded with the aid of nitrogen through a spinning nozzle, the filament cooled, cold drawn to 400% of the initial length, and wound on bobbins. The filament has a high whiteness value. The compounds of formulae 42 or 47 can be employed in place of the compound of formula 20 with equally good success.

APPLICATION EXAMPLE H

A melt of 1000 parts of caprolactam containing 30 parts of water and 0.8 parts of the brightening agent of formula 20 is reacted with stirring for 4 hours at 240° under pressure and subsequently for 1 hour with the pressure released. The melt is extruded through a slot die in ribbon form, chilled in water, cut into chips and dried. The dry polyamide 6 chips have an appreciably higher degree of whiteness than comparable chips containing no incorporated brightener. The compound of formula 1 may be employed in equivalent manner.

APPLICATION EXAMPLE J

A batch of polypropylene granules delustred with titanium dioxide is powdered in a mixer with 0.01 to 0.05% of its weight of the compond of formula 16. The granules are loaded into a melt spinning machine, melted at 310° under nitrogen and spun in filament form. The filament is hot drawn by the two-stage process. It shows an appreciably higher degree of whiteness than comparable filament containing no brightener.

Similar white effects can be obtained in this method of application with the compounds of formulae 19 and 20 in place of the compound of formula 16.

APPLICATION EXAMPLE K

A solution of 200 parts of polyvinyl chloride and 0.04 parts of the compound of formula 1 in methylene chloride is converted into filament by the wet spinning process. A brilliant white filament is obtained which has good light fastness. For this application the compounds of formulae 46 and 24 are equally as suitable as that of formula 1.

APPLICATION EXAMPLE L

200 Parts of polypropylene granules are powdered in a mixer with 0.04 parts of the compound of formula 19. After processing on a three-roll mill at 140° to 220°, the mixture is either moulded in the form of panels or regranulated and injection moulded in the desired form. The moulded products have a distinctly higher degree of whiteness than comparable products without a brightener additive.

If the compound of formula 17 or 38 is used in place of that of formula 19, similar white effects are obtained.

APPLICATION EXAMPLE M

100 Parts of polyester granules are powdered in a mixer with 0.02 parts of the compound of formula 1 and injection moulded. The moulded products are of superior appearance to products containing no incorporated brightener. In this Example the polyester granules can be replaced by other granulated materials, for example polyamide, polystyrene, polyethylene or cellulose acetate, on which white effects of similar quality are obtained; the same applies when the compound of formula 1 is replaced by the compound of formula 45.

APPLICATION EXAMPLE N

An amount of 0.01 to 0.05 parts of the compound of formula 20 is mixed with 100 parts of moulding material consisting of 65 parts of polyvinyl chloride, 35 parts of a plasticizer, e.g. dioctyl phthalate, and 2%, relative to the polymer, of a stabilizer. The mixture is processed on a multi-roll mill for 3 to 6 minutes at 165° to 185°, transferred to an extrusion moulding machine and extruded as film. If opaque film is desired, 2.5% titanium dioxide is incorporated in the mixture prior to processing.

The films are superior in appearance to films produced without a brightener additive.

APPLICATION EXAMPLE O

A mixture of 2 parts of the compound of formula 1,2 parts of a highly sulphonated castor oil, 8 parts of sodium dioctyl phenyl polyglycol etheroxy acetate containing 40 ethenoxy groups in the molecule and 80 parts of water is prepared. The mixture is ground in a suitable machine such as a sand mill until the major fraction of the particles is within the size range 0.5 to 2 microns.

20 Parts of the resulting dispersion, are dispersed in 1000 parts of water. The liquor is padded on a fabric of polyester fibre, e.g. polyethylene terephthalate, at room temperature and at an expression leaving the fabric with 80% of its weight of the liquor. The fabric is dried for 30 minutes at 60° and treated for 1 minute in dry heat at 220° for fixation. The fabric is strongly brightened.

This method of application can also be employed for the optical brightening of blend fabrics of 67 parts of polyethylene terephthalate and 33 parts of cotton, or of fabrics of polyester fibre of different composition, e.g. 1-4-dimethylocyclohexane terephthalate.

What we claim is:

1. A compound of the formula,

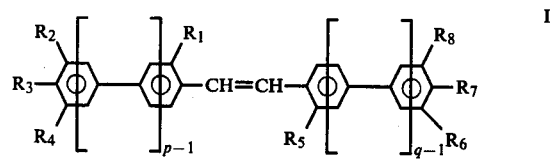

in which
$R_1$ and $R_5$ each signifies hydrogen or linear alkyl of 1 to 4 carbon atoms,
$R_2$, $R_3$, $R_4$, $R_6$, $R_7$ and $R_8$ each signifies hydrogen, halogen, alkyl or alkoxy of 1 to 8 carbon atoms, alkenyl of 3 to 8 carbon atoms, or -COOR',
in which R' signifies hydrogen, alkyl of 1 to 22 carbon atoms, hydroxyalkyl of 2 to 4 carbon atoms, phenyl or methyl- or chlorine-substituted phenyl,
p signifies an integer from 1 to 3, and
q signifies an integer from 1 to 3, provided that the total of p and q is 4, 5 or 6, at least one of
$R_3$ and $R_7$ being -COOR'.

2. A compound of formula I, according to claim 1, in which $R_1$ and $R_5$ each signifies hydrogen or methyl; and $R_2$, $R_3$, $R_4$, $R_6$, $R_7$ and $R_8$ each signifies hydrogen, fluorine, chlorine, methyl, methoxy, alkenyl of 2 to 4 carbon atoms, carboxyl or carboxylic acid alkyl ($C_{1-14}$) ester.

3. A compound according to claim 1, in which $R_2$, $R_4$, $R_6$ and $R_8$ signify hydrogen.

4. A compound according to claim 1 wherein $R_1$ and $R_5$ are hydrogen.

5. A compound according to claim 4 of the formula,

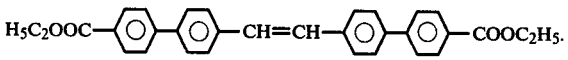

* * * * *